United States Patent
McNamara et al.

(10) Patent No.: US 8,715,348 B2
(45) Date of Patent: May 6, 2014

(54) METHOD AND DEVICE FOR STABILIZING JOINTS WITH LIMITED AXIAL MOVEMENT

(75) Inventors: Michael G. McNamara, Anchorage, AK (US); Avery B. Munoz, Eagle River, AK (US)

(73) Assignee: Alaska Hand Research LLC, Anchorage, AK (US)

( * ) Notice: Subject to any disclaimer, the term of this patent is extended or adjusted under 35 U.S.C. 154(b) by 1280 days.

(21) Appl. No.: 12/109,825

(22) Filed: Apr. 25, 2008

(65) Prior Publication Data

US 2008/0269743 A1 Oct. 30, 2008

Related U.S. Application Data

(60) Provisional application No. 60/913,975, filed on Apr. 25, 2007, provisional application No. 60/984,895, filed on Nov. 2, 2007.

(51) Int. Cl.
*A61F 2/08* (2006.01)

(52) U.S. Cl.
USPC ............ 623/13.14; 606/301; 623/21.11

(58) Field of Classification Search
USPC ........ 623/13.11–13.14, 21.11–21.19; 606/60, 606/232, 304, 305, 300–302; 403/374.1–374.4
See application file for complete search history.

(56) References Cited

U.S. PATENT DOCUMENTS

| | | | |
|---|---|---|---|
| 5,423,819 A | 6/1995 | Small et al. | 606/73 |
| 5,584,836 A | 12/1996 | Ballintyn et al. | 606/73 |
| 5,690,676 A | 11/1997 | DiPoto et al. | 606/232 |
| 5,718,706 A | 2/1998 | Roger | 606/73 |
| 5,944,724 A | 8/1999 | Lizardi | 606/104 |
| 6,139,565 A | 10/2000 | Stone et al. | 606/232 |
| 6,280,474 B1 | 8/2001 | Cassidy et al. | 623/16.11 |
| 6,517,564 B1 | 2/2003 | Grafton et al. | 606/213 |
| 6,524,317 B1 | 2/2003 | Ritchart et al. | 606/72 |
| 6,554,852 B1 | 4/2003 | Oberlander | 606/232 |
| 6,569,188 B2 | 5/2003 | Grafton et al. | 606/232 |
| 6,685,728 B2 * | 2/2004 | Sinnott et al. | 606/232 |
| 6,840,953 B2 | 1/2005 | Martinek | 606/232 |

(Continued)

FOREIGN PATENT DOCUMENTS

| | | | | |
|---|---|---|---|---|
| WO | WO 97/30649 | | 8/1997 | A61B 17/58 |
| WO | WO 02/36020 A1 | | 5/2002 | A61B 17/04 |

(Continued)

OTHER PUBLICATIONS

Authorized Officer—Philip Nice, International Search Report and Written Opinion; issued Aug. 28, 2008, PCT/US2008/061564; 18 pages.

*Primary Examiner* — Thomas J Sweet
*Assistant Examiner* — Christopher D Prone
(74) *Attorney, Agent, or Firm* — Sunstein Kann Murphy & Timbers LLP

(57) ABSTRACT

An apparatus for stabilizing a joint with low relative motion during orthopedic surgery. The apparatus includes a press-fit fastener body and a coupler. The press-fit fastener body has a proximal end and a distal end and is configured to be press-fit into a tunnel in a first bone member. The coupler is located on or is part of the press-fit fastener body and is configured to receive at least one flexible element trailing from at least one suture anchor. At least a portion of the suture anchors are located within a second bone member.

37 Claims, 10 Drawing Sheets

(56) References Cited

U.S. PATENT DOCUMENTS

| | | |
|---|---|---|
| 7,226,469 B2 | 6/2007 | Benavitz et al. ............... 606/232 |
| 7,235,079 B2 | 6/2007 | Jensen et al. .................... 606/73 |
| 7,588,587 B2 | 9/2009 | Barbieri et al. ............... 606/232 |
| 7,625,395 B2 | 12/2009 | Mückter ........................ 606/300 |
| 7,727,278 B2 * | 6/2010 | Olsen et al. ................. 623/13.12 |
| 7,951,198 B2 | 5/2011 | Sucec et al. ................. 623/13.11 |
| 2002/0022862 A1 | 2/2002 | Grafton et al. ................ 606/232 |
| 2003/0167072 A1 | 9/2003 | Oberlander ................... 606/232 |
| 2004/0127907 A1 | 7/2004 | Dakin et al. .................... 606/72 |
| 2004/0153074 A1 | 8/2004 | Bojarski et al. ................. 606/72 |
| 2005/0159812 A1 * | 7/2005 | Dinger et al. ............... 623/13.14 |
| 2005/0177167 A1 | 8/2005 | Muckter ......................... 606/73 |
| 2005/0283158 A1 | 12/2005 | West Jr. ......................... 606/73 |
| 2006/0189993 A1 | 8/2006 | Stone ............................. 606/73 |
| 2006/0276795 A1 | 12/2006 | Orbay et al. .................... 606/71 |
| 2007/0191708 A1 | 8/2007 | Gerold et al. ................. 600/431 |
| 2007/0213730 A1 | 9/2007 | Martinek et al. ................ 606/72 |
| 2007/0292820 A1 | 12/2007 | Canter .......................... 433/173 |
| 2008/0140118 A1 | 6/2008 | Martinek ...................... 606/232 |
| 2008/0147063 A1 | 6/2008 | Cauldwell et al. .............. 606/60 |
| 2008/0243184 A1 | 10/2008 | Martinek et al. .............. 606/232 |
| 2010/0076499 A1 | 3/2010 | McNamara et al. .......... 606/304 |

FOREIGN PATENT DOCUMENTS

| | | | |
|---|---|---|---|
| WO | WO 03/051205 A1 | 6/2003 | ............. A61B 17/04 |
| WO | WO 03/063713 | 8/2003 | ............. A61B 17/04 |
| WO | WO 2006/088359 | 8/2006 | ................ A61F 2/08 |
| WO | WO 2006/099109 | 9/2006 | ................ A61F 2/02 |
| WO | WO 2006/122218 A2 | 11/2006 | ............. A61B 17/58 |

* cited by examiner

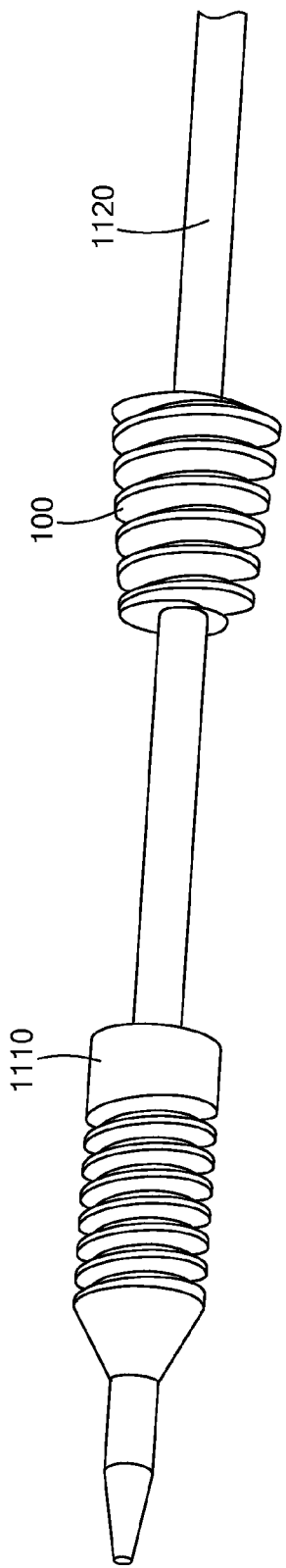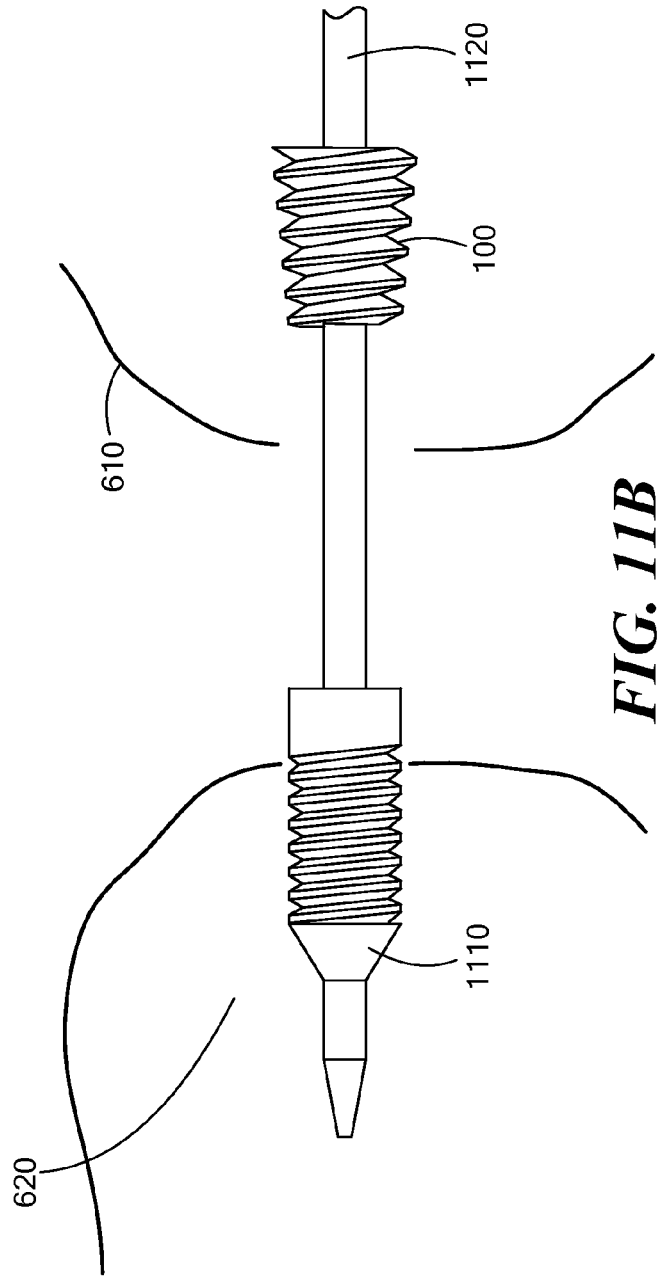

METHOD AND DEVICE FOR STABILIZING JOINTS WITH LIMITED AXIAL MOVEMENT

PRIORITY

This patent application claims priority from provisional U.S. patent applications:

Application No. 60/913,975, filed Apr. 25, 2007, entitled, "Method and Device for Securing Suture Anchors in Tension," and naming Michael G. McNamara and Avery B. Munoz as inventors, the disclosure of which is incorporated herein, in its entirety, by reference.

Application No. 60/984,895, filed Nov. 2, 2007, entitled, "Method and Device for Securing Suture Anchors in Tension," and naming Michael G. McNamara and Avery B. Munoz as inventors, the disclosure of which is incorporated herein, in its entirety, by reference.

FIELD OF THE INVENTION

The invention generally relates to joint surgery. More specifically, the invention relates to a method and device for stabilizing a joint with low relative axial motion.

BACKGROUND ART

Scapho-lunate dissociation is the most common carpal instability. Scapho-lunate dissociation can be characterized by diastasis between the scaphoid and lunate bones and rotatory subluxation of the scaphoid. Scapho-lunate dissociation typically causes wrist pain, swelling, clicking, progressive radiocarpal arthritis, and decreased motion and grip strength. There are currently many surgical treatment options that may be indicated depending on a variety of factors, including healing potential of the ligament, time elapsed since injury, alignment/reducibility of the carpal row and presence/extent of degenerative changes in the wrist. However, all of these treatments have some undesirable results (e.g., loss of range of motion, long periods of immobilization and/or high rates of failure). With the exception of the bone-tissue-bone grafts, each of the treatment options mentioned below have been used for over 10 years. Additionally, the bone-tissue-bone grafts and the RASL procedure discussed below have only limited clinical results.

One method used to treat scapho-lunate dissociation is dorsal capsulodesis. Dorsal capsulodesis can be performed with or without repair of the scapholunate interosseous ligament (SLIL). During either method, a physician temporarily pins Kirschner wires across the scapholunate and scaphocapitate intervals to restore proper carpal alignment during healing. Currently available results indicate that dorsal capsulodesis is associated with long term weakening and provides only limited motion recovery.

Bone-tissue-bone grafts are another treatment option for scapho-lunate dissociation. During the bone-tissue-bone graft procedure, the physician utilizes an autologous bone-tissue-bone graft to replace the scapholunate interval. Complications associated with bone-tissue-bone grafts include the problems associated with a second surgical site and selecting a graft that operates similarly to the SLIL being replaced. As stated above, the results of these treatments are variable and long term outcomes are unknown.

One of the newer and less invasive methods for treating Scapho-lunate dissociation is known as the Reduction and Association of the Scaphoid and Lunate (RASL) procedure. Although long-term results are unavailable, the RASL procedure offers only limited motion recovery and relatively high potential for failure. During failure, screws inserted into the bone during the procedure may back out and protrude into the scapho-lunate interval. In addition, the screws wear and weaken the bone as the bone rotates about the screw during motion. Once a RASL procedure fails the patient is left with very limited treatment options because the damage to the bone is typically very severe.

Chronic instances of scapholunate instability extending towards degenerative arthritis typically require more extreme surgical procedures with highly compromising results. One such option is intercarpal fusion. During the intercarpal fusion procedure, a physician fuses two or more carpal bones (e.g., scapholunate, scaphoid-trapezium-trapezoid, scaphoid-capitate-lunate, and lunate-capitate-triquetrum-hamate) together. As one would expect, fusion of the bones greatly reduces the patient's range of motion. Additionally, there are high complication and failure rates associated with the intercarpal fusion procedure.

Suture anchors are well-known in the prior art and are commonly used by physicians to secure soft tissue to bone. A suture anchor typically includes a body portion and at least one suture secured to the body portion. The body portion is driven into the bone, and a securing means secures the body portion within the bone. For example, many suture anchors have threads, screws, hooks, or deployable members located on the body portion.

In practice, a physician typically drills a hole into a bone. The physician then inserts (e.g., screws, threads, etc.) the body portion of a suture anchor into the bone tunnel. The suture(s) is then secured to the soft tissue (e.g. ligament) using any of a number of methods (e.g., knotting, tying, looping, etc.), depending on the design of the suture anchor being used. Because a suture anchor includes a suture attached to the body portion, the suture anchor secures the ligament to the bone.

SUMMARY OF THE INVENTION

In various embodiments of the present invention, an apparatus for stabilizing a joint with low relative axial motion during orthopedic surgery includes a fastener body and a coupler. The fastener body has a proximal end and a distal end and is configured to be press-fit into a tunnel in a first bone member. The fastener body may also be cannulated. The coupler may be located on or may be part of the fastener body. The coupler can receive at least one flexible element trailing from at least one suture anchor. At least a portion of the suture anchor may be located within a second bone member. In some embodiments, the first bone member is a scaphoid bone and the second bone member is a lunate bone. However, in alternative embodiments, the first bone member is a lunate bone and the second bone member is a scaphoid bone.

The fastener body may be tapered from the proximal end to the distal end such that the width of the distal end is approximately equal to a major diameter of the suture anchor. The fastener body may also be non-tapered. The proximal end of the fastener body may include a proximal indentation. The flexible element(s) is/are secured to the fastener body at the proximal indentation.

The coupler can be a channel extending along an outer surface of the fastener body from the proximal end to the distal end. Alternatively, the coupler may be an eyelet. The apparatus can be made from a variety of materials including, but not limited to, polymeric material, titanium, or bone, or a bioabsorbable material. The fastener body may include a receptacle configured to receive a hexagonal driver.

In other embodiments of the present invention, a method of securing a suture anchor includes inserting a suture anchor into a first bone member, securing a flexible element attached at one end to a fastener, inserting the fastener into a hole in a second bone member, and adjusting the flexible member to a desired tension. The flexible element can have a first end and a second end and may be attached to the suture anchor at the first end. Alternatively, the flexible element can be threaded over or through the fastener. For example, the fastener may have a hole through the body. The physician can thread the flexible element through the hole, or the fastener may be supplied to the physician "pre-loaded" (e.g. the flexible element may already be coupled to the fastener). The physician may then adjust the flexible element to the desired length. During installation of the suture anchor, the flexible element may span a space between the first bone member and a second bone member and pass through the tunnel in the second bone member so that it may be secured to the fastener. The fastener may be configured to be press-fit into the tunnel in the second bone member. As the physician adjusts the flexible member to a desired tension, the first bone member is secured to the second bone member. Inserting the fastener into the tunnel in the second bone member may create the press-fit. Additionally, the fastener may include at least one thread configured to facilitate the removal of the apparatus from, or adjustment of the apparatus within the second bone member. An example of the thread located on the fastener is a screw thread (e.g., a raised helical rib).

In still other embodiments, the method may include drilling a hole through at least the first bone member and the second bone member. The first bone member can be a lunate bone and the second bone member can be a scaphoid bone. The first and second bone members can be bone fragments or any other bone material.

The suture anchor can be inserted such that the suture anchor is beneath the surface of the first bone member. Likewise, the fastener can be inserted such that it is beneath the surface of the second bone member. By inserting the suture anchor and fastener in this manner, abrasion of and by adjacent bone and soft tissue is avoided.

The steps of the method can occur in a variety of orders. For example, securing the flexible element may occur before inserting the fastener and adjusting the flexible member. Alternatively, inserting the fastener can occur before securing the flexible element and adjusting the flexible member. Additionally, adjusting the flexible member may occur before securing the flexible element and inserting the fastener. The suture anchor and fastener may also be supplied such that they are both already coupled to the flexible element. The anchor and fastener may be cannulated for placement over a guide wire.

In still other embodiments, a kit for use during orthopedic surgery to couple bone members includes at least one suture anchor, a fastener, and at least one flexible element. The suture anchor can be for insertion into a first bone member. The fastener can have a fastener body, and a coupler located on or as a part of the fastener body. The fastener may be configured to be press fit into a hole in a second bone member and the fastener may be threaded as described above. The at least one flexible element may have a first end and a second end. The first end may be attached to the suture anchor and the second end may be configured to be secured to the fastener body, thereby placing the flexible element in tension and coupling the first and second bone members. In embodiments containing multiple suture anchors, more than one suture anchor may be attached to a single fastener.

The first bone member can be a scaphoid bone and the second bone member can be a lunate bone. Alternatively, the first bone member can be a lunate bone and the second bone member can be a scaphoid bone.

The fastener body can be tapered from a proximal end to a distal end such that the width of the distal end is approximately equal to the major diameter of the suture anchor. The proximal end of the fastener body can include a proximal indentation, at which the at least one flexible element is secured to the fastener body. The coupler can be a channel extending along an outer surface of the fastener body from a proximal end to a distal end. Alternatively, the coupler can be an eyelet. The flexible element may be any suture material available on the market, and may be coupled with soft tissue implants or similar.

The suture anchor and fastener can be made from a variety of materials including, but not limited to a polymeric material, titanium, bone, or a bioabsorbable material. Non-metallic versions of this device may be manufactured with a small "chip" of biocompatible metal to serve as a radio-opaque marker to be viewable on x-ray. The fastener body may include a receptacle configured to receive a hexagonal driver.

This invention greatly broadens applications of suture anchors in orthopedics, extending the focus to fixture of bone to bone, rather than just soft tissue to bone.

BRIEF DESCRIPTION OF THE DRAWINGS

The foregoing features of the invention will be more readily understood by reference to the following detailed description, taken with reference to the accompanying drawings, in which:

FIGS. 11A and 11B schematically show alternative embodiments of a system utilizing a cannulated suture anchor and fastener, in accordance with embodiments of the present invention.

DETAILED DESCRIPTION OF SPECIFIC EMBODIMENTS

Figure 1:
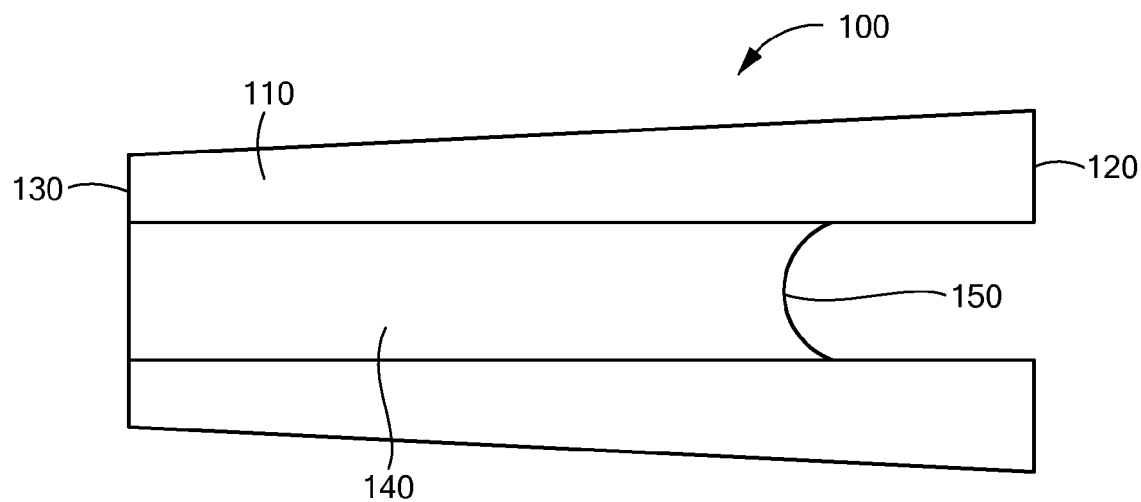
FIG. 1 schematically shows a side view of the device for coupling two or more bones in accordance with embodiments of the present invention.
Figure 2:
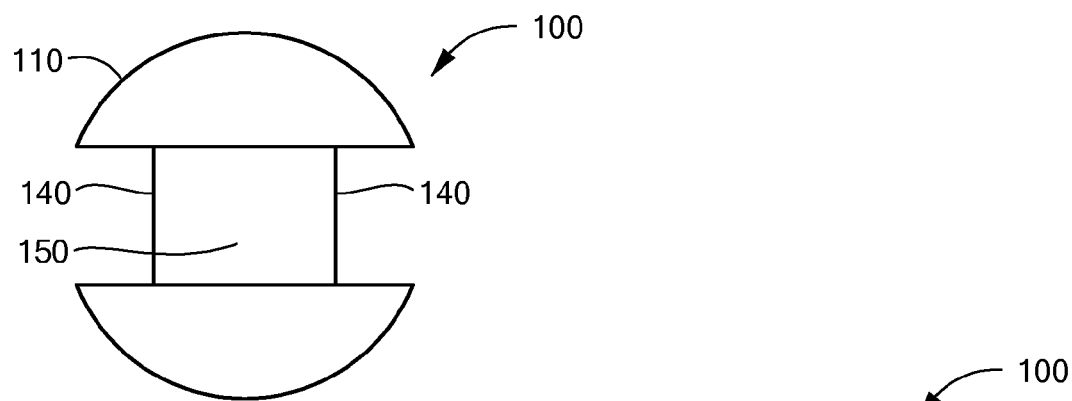
FIG. 2 schematically shows a proximal view of the device shown in FIG. 1.
Figure 6:
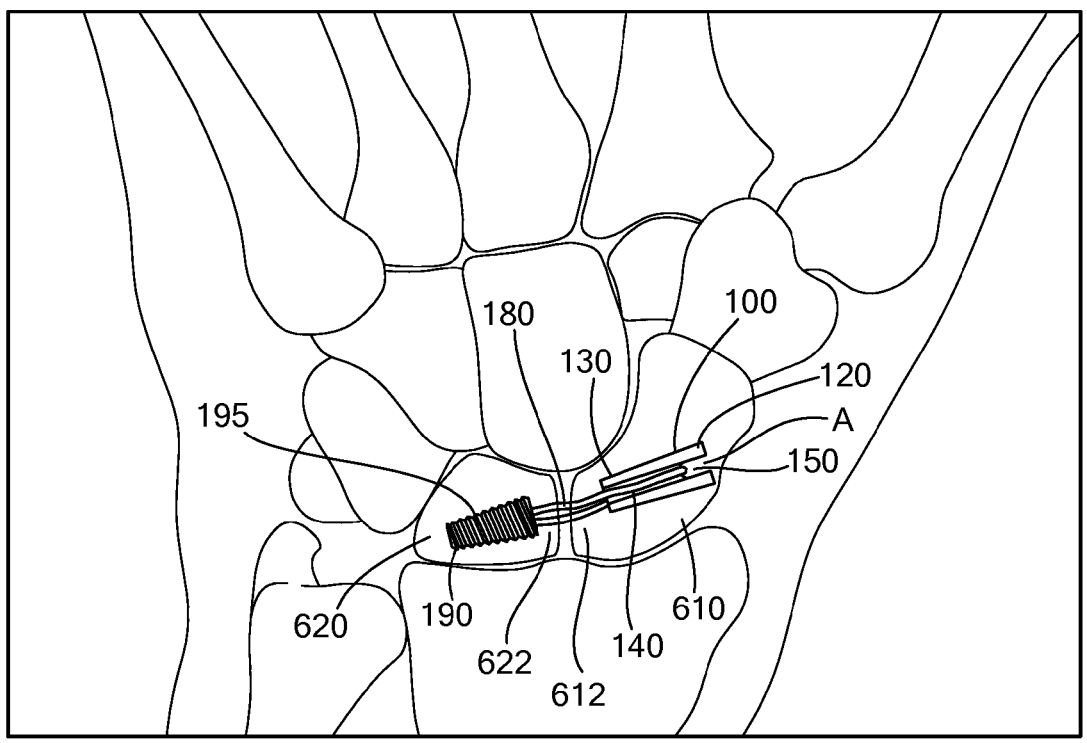
FIG. 6 schematically shows the device of FIG. 1 securing a scaphoid bone and lunate bone within a patient's hand.

Referring now to FIG. 1, a press-fit fastener 100 for coupling two or more bones in tension greatly simplifies and improves upon the currently used methods for controlling relative motion between bones or inter-fragmentary stabilization. The device (and method for using the same), when used in conjunction with a suture anchor 190 (FIG. 6), creates a system for adjustably securing a suture anchor 190 in tension. The system gives a physician the ability to manipulate movement between at least two bone members in a joint with low relative axial motion. The system also allows a physician to secure inter-fragmentary stabilization of a bone fracture. The system is used in conjunction with a suture anchor 190 to offer adjustable tension, thereby controlling the position (e.g., alignment), amount of rotation, and resistance to shear. The amount of desired rotation and shear depend on the application.

This system broadens the field of applications in which suture anchors can be used and allows physicians to address and solve current challenges in orthopedics. As mentioned above, suture anchors currently affix soft tissue to bone. Embodiments of this invention allow a physician to secure bone to bone. Further, proper use of embodiments of this device (involving connection of the device to a suture anchor) offers temporary or permanent fixation, restoration of carpal alignment, and normal range of motion between the scaphoid and lunate bones. For acute ligament tears, the tears and bones may be valuated, aligned, and debrided using a scope. Additionally, for chronic scapho-lunate tears, the procedure may be preceded by excision of part of the scapho-lunate joint using the RASL (Reduction and Association of the Scaphoid and Lunate) technique. As is known in the art, the RASL procedure can be performed percutaneously or through a limited incision and arthroscopic assist. In either RASL method, the articular surfaces of the scapho-lunate joint are excoriated to expose cancellous bone. The scaphoid and the lunate are then reduced using "K-Wire Joysticks" (typically 0.062"). A cannulated screw is passed over a K-wire, through the scaphoid, across the joint, and into the lunate. The methods in accordance with embodiments of the present invention may utilize techniques defined by the RASL procedure to excoriate the articular surfaces and properly align the scaphoid and lunate prior to inserting the suture anchor 190 and press-fit fastener 100.

The use of a suture anchor 190 and press-fit fastener 100, as described below, does not suffer from the problems associated with the RASL procedure described above. The flexible element 180 extending between the scaphoid and lunate more closely mimics the characteristics of the scapholunate ligament. Additionally or alternatively, as described in greater detail below, the device may be implanted with autograft, allograft, or xenograft tissue, allowing early range of motion coupled with stabilization of the joint during healing. Therefore, mobility is not impaired and the patient can mobilize the hand and wrist immediately.

Although the invention is described with respect to the scaphoid and lunate bones, the invention may be used to position and secure other bones. A physician may use embodiments of this invention to treat injuries at other articular surfaces throughout the body that experience limited relative motion. Such articular surfaces may include the acromioclavicular joint, as well as joints between the tarsals, metatarsals, other carpal bones and metacarpals. Some embodiments may also be used to stabilize bone fragments while healing occurs. In such embodiments, the physician may insert and secure a suture anchor 190 (see FIG. 6) in one fragment, and the fastener in at least one other. The physician may then tie off a flexible element 180, attached to the suture anchor 190, onto the fastener at the desired tension. The purpose of the device in this application is to maintain good contact and alignment between bone fragments while healing occurs.

As shown in FIG. 1, the press-fit fastener 100 can have a main body 110 that is shaped and sized such that it may achieve an interference fit (e.g., a press fit) with the tunnels/drill holes created by the physician, as discussed in greater detail below. An interference fit, sometimes called press fit, is a method of fastening two parts by creating friction between the parts as they are pushed together. In embodiments of this invention, a physician can push the press-fit fastener 100 into a tunnel in the bone, and the resulting compression and tensile forces between the press-fit fastener 100 and bone hold the press-fit fastener 100 in the bone. In some embodiments, the main body 110 of the press-fit fastener 100 can be tapered such that it has a generally decreasing cross section from the proximal end 120 to the distal end 130. In some embodiments, the width at the distal end 120 is approximately equal to the major diameter of the suture anchor 190. This helps to form the interference fit between the implantable press-fit fastener 100 and the bone and secure the location of the device in bone.

Figure 8:
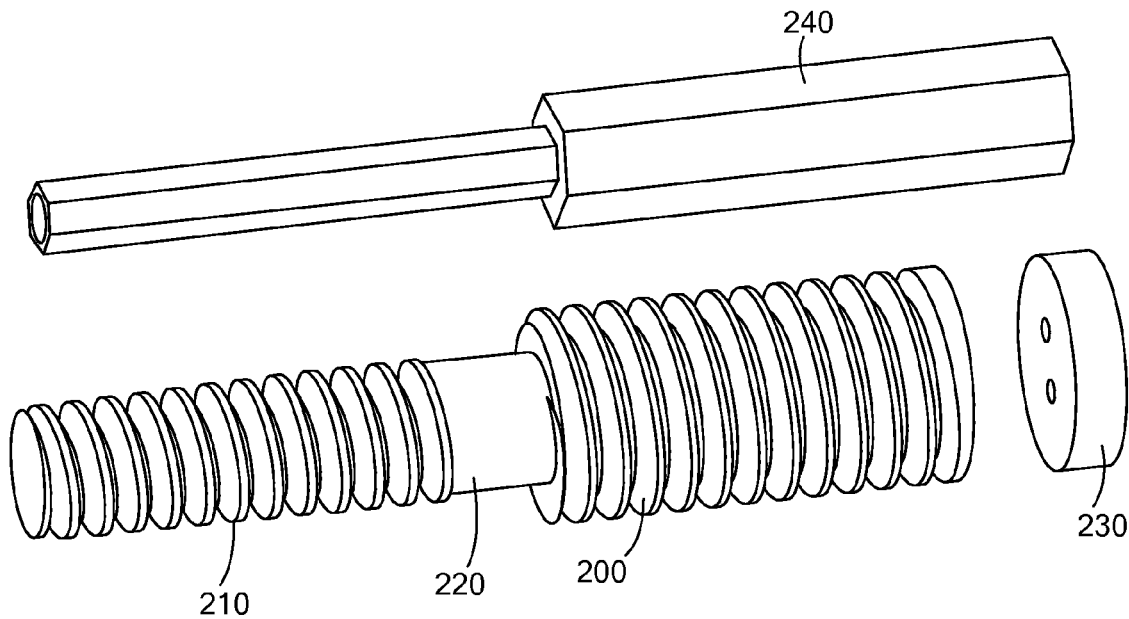
FIG. 8 schematically shows another alternative embodiment of a system to secure bone members, including a stepped driver.

The embodiment of the press-fit fastener 100 shown in FIG. 1 does not include a head at the proximal end 120. However, the press-fit fastener 100 may include a head (not shown) that can sit deep to or on top of the articular surface. Additionally, the press-fit fastener 100 may include a receptacle for a hexagonal driver 240 (FIG. 8). In such embodiments, the physician can use the hexagonal driver 240 to insert and/or remove the press-fit fastener 100 from the bone member.

As mentioned above, the physician can use the press-fit fastener 100 in conjunction with a suture anchor 190 to secure the suture anchor 190 and flexible element 180 in tension. Although the below discussions refer to suture anchors 190 with threads 195 and a flexible element 180, the press-fit fastener 100 can be used in conjunction with any number of types of suture anchors. For example, the suture anchor 190 can have deployable members (rather than threads) that secure the suture anchor 190 within the hole in the bone member. Further, the flexible elements 180 can be separate elements that need to be attached to the suture anchor 190 or they may come pre-attached or integral to the suture anchor 190. Additionally, the flexible elements 180 can be threaded over or through the anchor 190. For example, the anchor 190 may have a central bore similar to one embodiment of the coupler described below. The flexible elements 180 can be threaded through the central bore and tied off at the opposing end of the suture anchor 190. In some embodiments, the suture anchor 190 can also have a cap 230 (FIG. 8) to which the flexible element 180 can be tied or otherwise attached.

To secure the suture anchor 190 in tension, the flexible element 180 extending from the suture anchor 190 can be coupled to the press-fit fastener 100. The press-fit fastener 100 may include a coupler that facilitates the coupling of the flexible element 180 to the press-fit fastener 100. The coupler can be a separate element located on or integral with the press-fit fastener 100 (e.g., an eyelet) or it can be integral to the fastener body 100 (e.g., the channels 140 discussed below).

In one embodiment of the present invention, the coupler can be channels 140 extending from the proximal end 120 to the distal end 130 of the main body 110. As discussed in greater detail below, the channels 140 provide an indentation in which the flexible element 180 can sit without interference or abrasion from surrounding bone and tissue. The coupler can also include a concavity 150 located at the proximal end 120 of the main body 110 and a concavity 170 located at the distal end 130 of the main body 110. The flexible element 180 can be secured to the press-fit fastener 100 at the concavity 150. The flexible element 180 can be secured to the press-fit fastener 100 at the concavity 150 by tying the flexible element 180 into a knot, capping, crimping, brazing, welding or any other suitable means.

Figure 3:
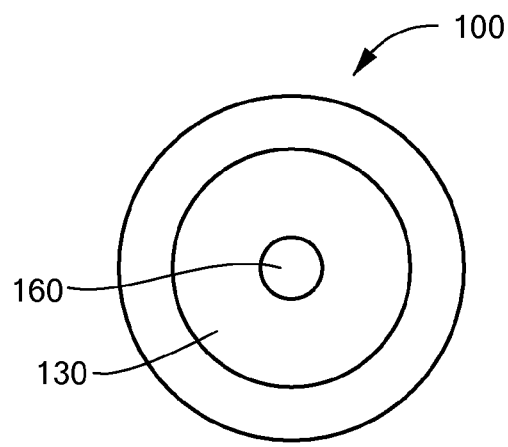
FIG. 3 schematically shows a distal view of an alternative embodiment of the device shown in FIG. 1.
Figure 4:
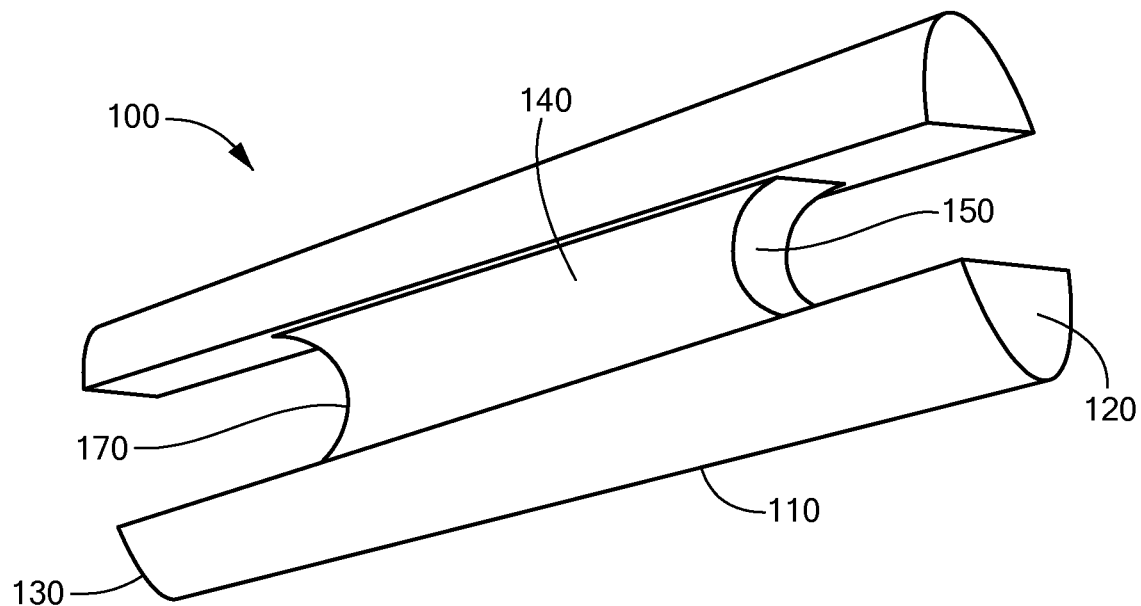
FIG. 4 schematically shows an isometric view of an alternative embodiment of the device for securing suture anchors in tension.

In other embodiments of the present invention, the coupler can be a central bore 160 (FIG. 3) through which the flexible element 180 is passed. Once the flexible element 180 is passed through the central bore 160, it can be secured using any of the embodiments discussed above. In a similar manner as the channel embodiment discussed above, embodiments having a central bore 160 can also have a concavity 150 at which the flexible element can be secured. In some embodiments, the press-fit fastener 100 can also have an eyelet or a "T" (not shown) around which the flexible member(s) 180 can be secured. The eyelet may be a hole within either the suture anchor 190, the fastener 100, or the coupler. Additionally or alternatively, the eyelet may be a ring attached to or integral with the suture anchor 190, the fastener 100, or the coupler.

In further embodiments of the present invention, the press-fit fastener 100 need not have either the channels 140 or the central bore 160. In such embodiments, the interference fit (e.g., the press-fit) between the press-fit fastener 100 and the tunnel in the bone act to secure the flexible element 180 to the press-fit fastener 100. Specifically, as the press-fit fastener 100 is inserted into the tunnel within the scaphoid bone 610 (FIG. 6), the flexible element 180 is "pinched" between the main body 110 and the wall of the tunnel, securing the flexible element 180 in place.

Regardless of the type of coupler, embodiments of the present invention that utilize the combination of the suture anchor 190 and the press-fit fastener 100 are beneficial because they provide physicians with highly adjustable systems for securing and tensioning bones and suture anchors. The physician can adjust and secure the flexible element 180 without interference from the other system components (e.g., the suture anchor 190 and press-fit fastener 100) or the bones in which the system components are inserted. In addition, because certain embodiments of the present invention utilize an interference fit, the flexible element 180 does not become twisted, entwined, or entangled.

Figure 5A:
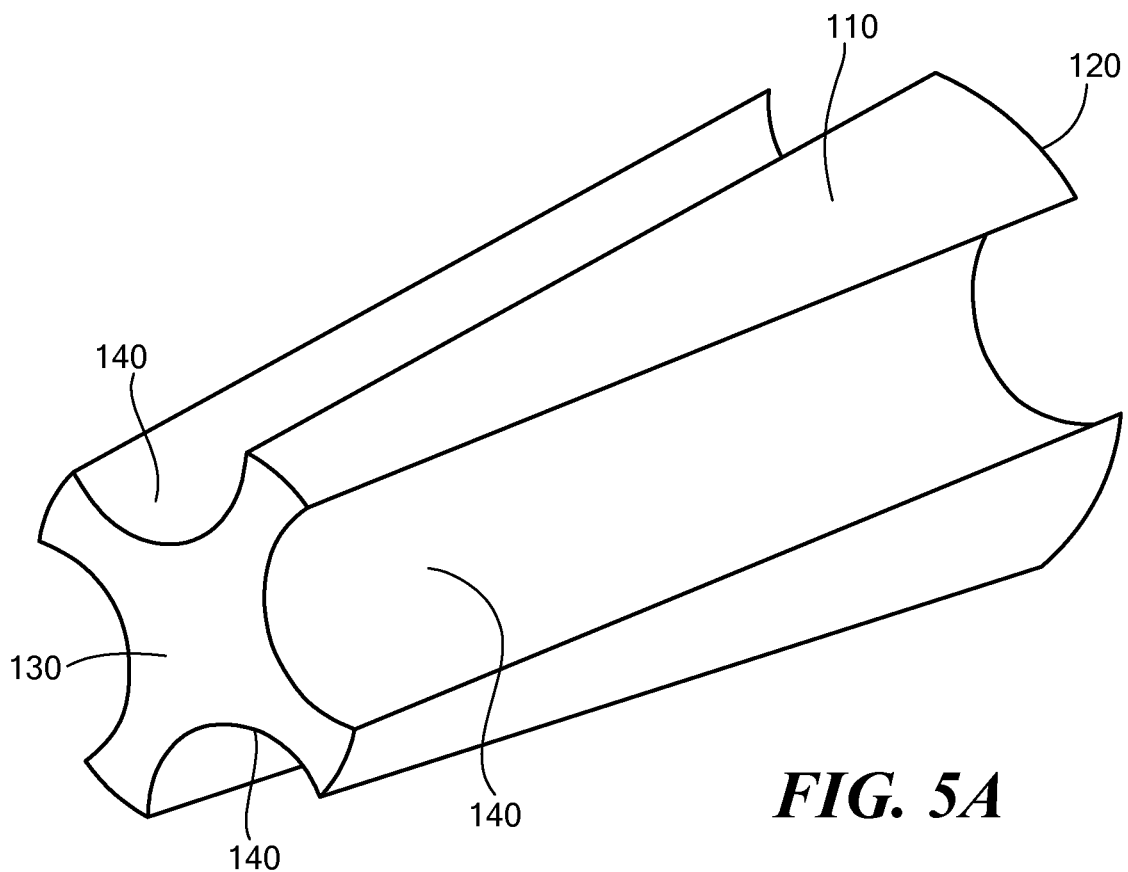
FIG. 5A schematically shows an isometric view of another alternative embodiment of the device for securing suture anchors in tension.
Figure 5B:
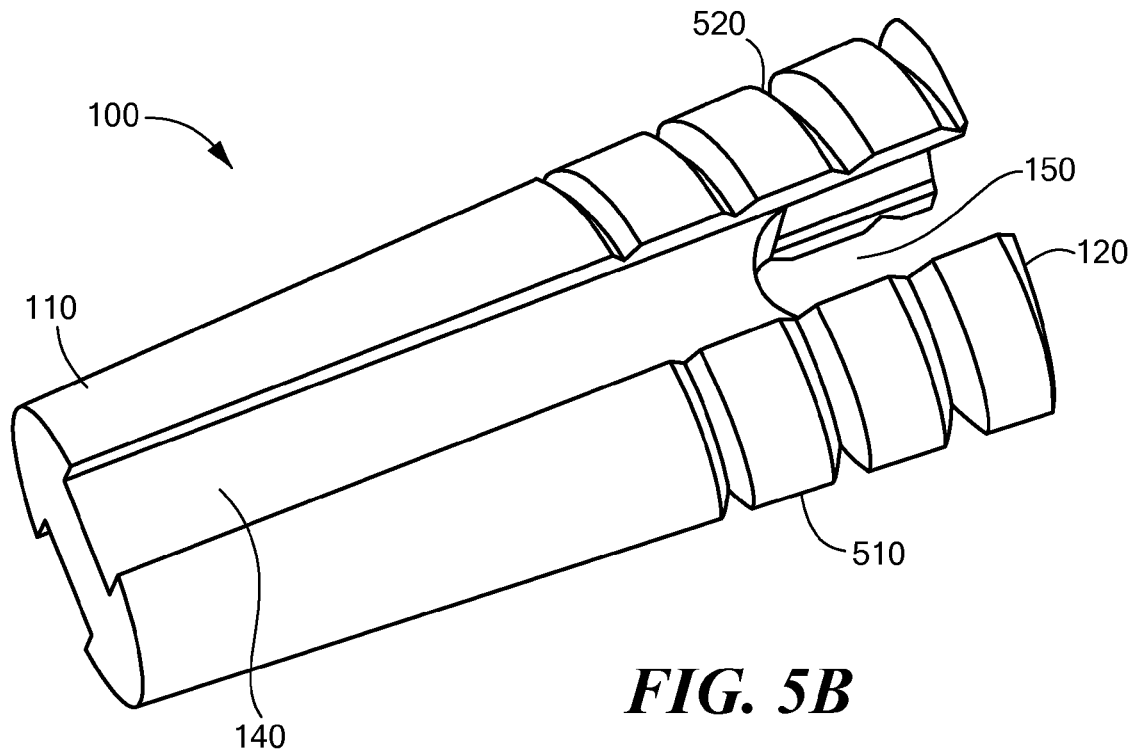
FIG. 5B schematically shows an isometric view of an alternative embodiment of the device for securing suture anchors in tension, wherein the device includes threads. The threads have a reverse-cutting edge for removal of the device from bone.
Figure 5C:
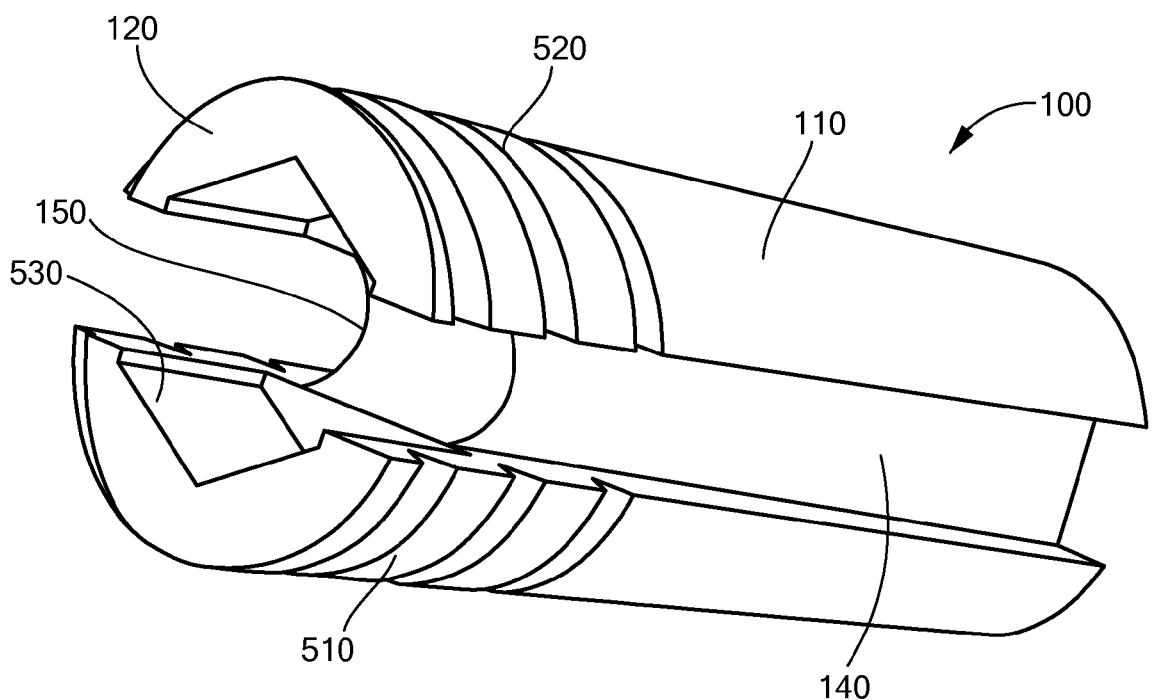
FIG. 5C schematically shows an proximal isometric view of the alternative embodiment of FIG. 5B.

As shown in FIGS. 5B and 5C, some embodiments of the press-fit fastener 100 can include one or more threads on the exterior of the tapered main body 110. The threads can be a raised helical rib, similar to a screw thread. Alternatively, the threads can be back cutting threads 510 that have the same outer dimension as the fastener (e.g., they are not raised above the surface of the fastener). The press-fit fastener 100 can be fully or partially threaded (FIGS. 5B and 5C show a partially threaded embodiment). The back cutting threads 510 (e.g., revision threads) may be very steep angled threads that are cut into the surface of the press-fit fastener 100. The cutting edge 520 of the back cutting threads 510 may be located toward the proximal end 120 so that the threads only engage during removal and revision of the press-fit fastener 100. The design of the threads 510 allows the press-fit fastener 100 to be easily removed and adjusted after it is inserted into the tunnel.

The back cutting threads 510 are for revision and removal purposes and are not intended to engage the bone member when the press-fit fastener 100 is inserted. Further, because the back cutting threads 510 are not raised above the surface of the press-fit fastener 100, they do not interfere with the press-fit between the press-fit fastener 100 and the tunnel.

The press-fit fastener 100 may also have a driver slot 530 to allow a physician to remove or adjust the press-fit fastener 100. For example, if the physician feels that the tension on the suture anchor 190 needs to be adjusted, the physician can use a driver to either further insert or back-out the press-fit fastener 100. In addition, the physician can use the driver to remove the press-fit fastener 100 once the bone and/or ligaments have healed. FIG. 5C shows a hexagonal recess, however other recess shapes (including a simple slot) are within the scope of this invention.

In other embodiments, the channels 140 can include a sharp cutting edge that acts in a similar manner to the revision threads 510 described above. Like the revision threads 510, the sharp cutting edge can be used to remove the press-fit fastener 100 from the bone. The channels 140 may also be formed in a cork-screw fashion wrapping around the surface of the press-fit fastener 100 (as opposed to the substantially linear orientation shown in FIGS. 5B and 5C). In either embodiment, the press-fit fastener 100 may include a driver slot located on the proximal end, similar to that shown in FIG. 5C.

Figure 7:
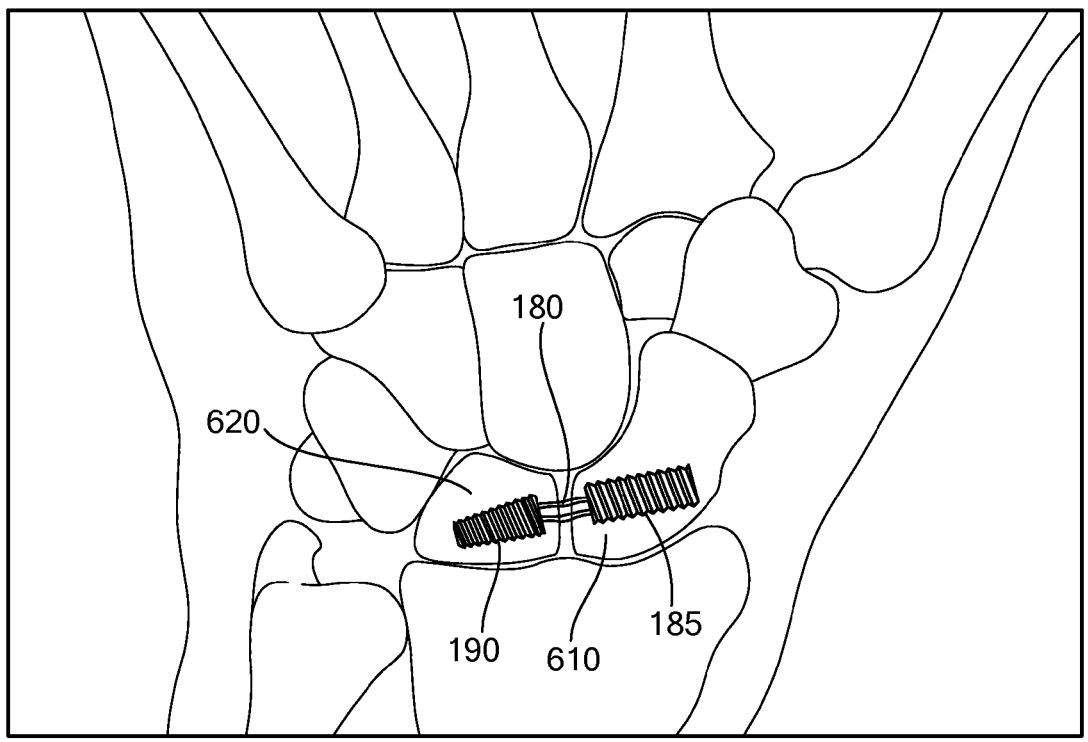
FIG. 7 schematically shows an alternative embodiment of a system to secure bone members.

FIGS. 7 and 8 show alternative embodiments of the present invention. As shown in FIG. 7, the press-fit fastener 100 may be replaced with a second suture anchor 185. Therefore, in this embodiment, the first suture anchor 190 is located within the lunate bone 620 and the second suture anchor 185 is located in the scaphoid bone 610. The flexible member 180 connects the two suture anchors and secures and stabilizes the scaphoid 610 and lunate 620.

As shown in FIG. 8, a sleeve 220 can cover the flexible element between the suture anchors 200 and 210 (or the suture anchor 190 and press-fit fastener 100). The sleeve protects the flexible element from abrasion from the adjacent bone and soft tissue and protects the adjacent bone and soft tissue from abrasion by the flexible element. Additionally, the device can have a cap 230 for securing the flexible member at the proximal end of the second suture anchor 200. The suture anchors 200 and 210 can be inserted into and removed from the bone members using the stepped driver 240. Although FIG. 8 shows two suture anchors 200 and 210, the stepped driver 240 and the cap 230 can be used in embodiments having a press-fit fastener 100.

Figure 9:
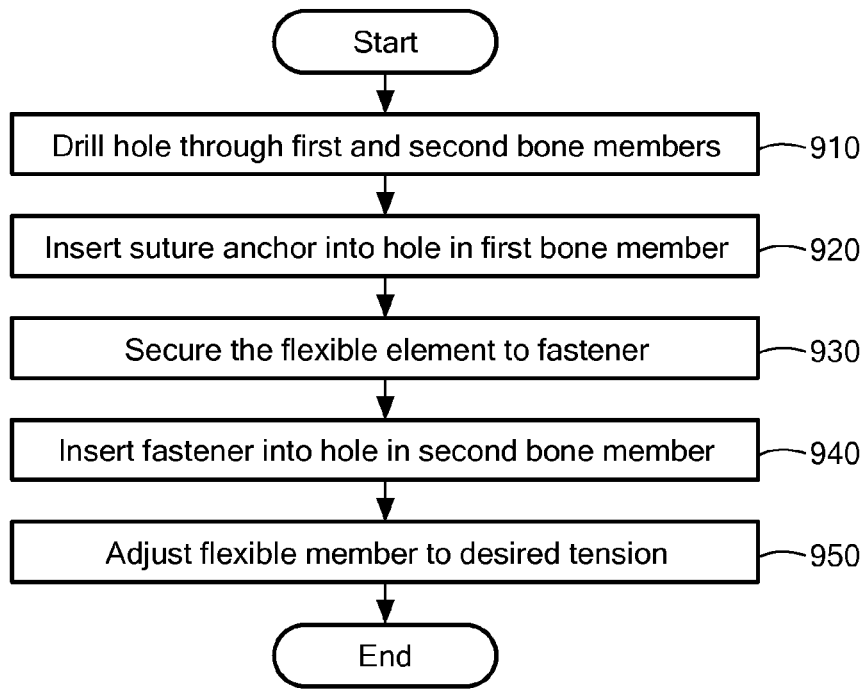
FIG. 9 is a flowchart showing the steps for using the device shown in FIG. 1.

FIG. 9 provides a flow chart of one method of using the press-fit fastener 100 to secure a suture anchor 190 in tension. First, the physician drills a hole (e.g., tunnel) through the bone members that need to be secured and/or stabilized. (step 910). For example, in the case of scapho-lunate dissociation, the physician would drill through the scaphoid bone 610 within the hand, FIG. 6.

A physician may use a variety of drilling procedures and drill bit types to drill the required holes/tunnels within the bone members. For example, the physician may separately drill two distinct holes (e.g., one in the first bone and one in the second bone). Alternatively, the physician may use a cannulated drill with a guide tip. In such embodiments, the physician may perform a first drill pass through one bone member (e.g., the scaphoid) and into the other (e.g., the lunate) using a drill bit with the diameter required to insert the anchor 190. Once the suture anchor 190 is inserted, the physician can then pass the flexible member 180 through the cannulated drill-bit and drill a larger hole/tunnel in the second bone member (e.g., over-drill the hole already in the scaphoid) such that it can receive the press-fit fastener 100. The guide tip will ensure that the holes are properly aligned. Alternatively, the second (larger) hole may be drilled prior to insertion of the suture anchor. In certain applications (e.g. self-drilling, cannulated suture anchor), as described in greater detail below, a single drill bit may be sufficient for drilling through a first bone member. The anchor may pass through the tunnel provided, and the fastener may create the press-fit in the same tunnel.

In addition, the physician may use a stepped drill bit. The stepped drill bit may have two separate diameters. For example, the stepped drill bit may have a smaller diameter portion located near the tip of the drill bit (e.g., for drilling the hole required for the suture anchor 190) and a larger diameter located at the base (e.g., for drilling the tunnel/hole required for the press-fit fastener 100). The stepped drill bit allows the physician to drill different size holes in the first bone member and the second bone member in a single pass. The stepped drill bit may include a tapered transition from the smaller to the larger diameter. All drills may be cannulated, or the system may make use of a parallel drill guide.

Once the physician has drilled the hole/tunnel through appropriate bone and/or ligaments (e.g., the scaphoid 610), the physician can insert the suture anchor 190 into the first bone member (e.g., the lunate 620) (step 920). All activities performed by the physician may take place through a single incision, and along axis A (see FIG. 6). Therefore, when inserting the suture anchor, the physician should insert the suture anchor 190 through the hole (e.g., transosseous tunnel) in the second bone member (e.g., the scaphoid 610). Doing so will ensure that the flexible member 180 will span the space between the first and second bone members (e.g., the scaphoid 610 and lunate 620) and pass through the hole in the second bone member (e.g., the scaphoid 610).

The physician can then secure the flexible member to the press-fit fastener 100. (Step 930) using the coupler (e.g., channels 140 or central bore 160). As mentioned above, the flexible member 180 can be secured to the press-fit fastener 100 in a variety of ways. Once the flexible member 180 is secured to the press-fit fastener 100, the press-fit fastener 100 can then be inserted into the hole in the second bone member (e.g., the scaphoid 610) (step 940). As mentioned above, the press-fit fastener 100 is designed such that it can be press-fit into the hole. Therefore, no additional tapping is required to insert the press-fit fastener 100. The physician need only press the press-fit fastener 100 into the tunnel.

Next, the physician can adjust the flexible member 180 to the desired tension (step 950). If the suture anchor 190 includes an internal locking mechanism (not shown), the physician can lock the flexible member 180 in tension using the internal locking mechanism. Otherwise the physician can tie or otherwise secure the flexible member to the anchor 190. By adjusting the flexible member 180 to the desired tension, the press-fit fastener 100 is secured in the second bone member and is prevented from backing out. Also, as the flexible member 180 is adjusted, the bone members will be secured and stabilized in the desired locations. For example, if the purpose of the suture anchor 190 and press-fit fastener 100 is to aid in healing between bone fragments, the suture anchor 190 and press-fit fastener 100 will cause the bone fragments to maintain contact and alignment during healing. Similarly, if the purpose is treatment of scapho-lunate dissociation, the suture anchor 190 and press-fit fastener 100 will permanently or temporarily fix and restore carpal alignment, while allowing substantially normal range of motion between the scaphoid bone 610 and lunate bone 620 while the ligaments heal.

The physician chooses the length of the flexible member 180 (e.g., the physician can adjust the length of the flexible member 180) such that it will allow a flexible rotational connection and proper alignment between the suture anchor 190 in the first bone member and the press-fit fastener 100 in the second bone member. To achieve inter-fragmentary stabilization, the physician should draw (e.g., adjust) the flexible element 180 trailing from the suture anchor 190 tight enough to hold the proximal surface 622 of the first bone fragment in good contact with the distal surface 612 of the second bone fragment, in which the press-fit fastener 100 is secured.

All of the embodiments may include placement of soft tissue (autograft, allograft, xenograft or similar) alongside the device. This allows for the device to provide stabilization and early range of motion to the bones while securing the soft tissue within the bone tunnel for incorporation into the joint.

Although the above described method is described as securing a single suture anchor 190 to a press-fit fastener 100, multiple suture anchors 190 can be secured to a single press-fit fastener 100. For example, some applications may require that multiple suture anchors be placed within the first bone member. In such applications, the physician does not necessarily need to use multiple fasteners 100. Rather, the physician can secure all of the suture anchors 190 and flexible elements 180 to a single press-fit fastener 100, greatly simplifying the procedure and reducing the procedure time. Specifically, the inherent "play" within the joint and the larger drill hole in the scaphoid 610 allow a physician to adjust the location and angle of the suture anchors 190 at the lunate 620. Therefore, after the physician passes the suture anchor 190 through the scaphoid 610 and the suture anchor 190 is at the surface of the lunate 620, the physician can move the suture anchors 190 to a new location (e.g., the physician can move them "north" or "south" because the width of the drill hole is larger than the width of the suture anchor and the inherent play in the joint) and insert them into the lunate. The physician can then bring the flexible elements 180 from each of the suture anchors 190 through the scaphoid tunnel and couple them to a single press-fit fastener 100 using the methods described above.

It is important to note that, although the method is described as being performed in a specified order, the order of the method steps can be rearranged and still accomplish substantially similar results. For example, the physician can insert the press-fit fastener 100 into the hole (step 940) prior to securing the flexible element 180 to the press-fit fastener 100 (step 930) and adjusting the flexible element 180 (step 950). Alternatively, the flexible element can be adjusted (step 950) prior to securing it to the press-fit fastener 100 (step 930) and inserting the press-fit fastener 100 into the hole (step 940).

Returning to FIG. 6, the press-fit fastener 100 and suture anchor 190 are shown in place and secured within a hand. The press-fit fastener 100 is located within the hole in the scaphoid bone 610, and the suture anchor is located in the hole in the lunate bone 620. The flexible element 180 extends between the press-fit fastener 100 and the suture anchor 190 and is secured within the channels 140 and the concavity 150 located at the proximal end 120 of the press-fit fastener 100. The suture anchor 190, press-fit fastener 100, and flexible element 180 work together to secure and stabilize the scaphoid 610 and lunate 620 during healing without limiting the patient's range of motion.

It is important to note that, although the above described embodiments are securing at least one flexible element from a suture anchor in tension, other embodiments within the scope of this invention can have a flexible member 180 (e.g., the loop) that extends from the suture anchor 190 in the form of a loop (not shown). In such embodiments, the physician can adjust the length of the flexible member 180 by manipulating an internal locking mechanism within a suture anchor 190. Alternatively, the flexible member 180 may be attached to the suture anchor 190 in such a way as to allow the physician to simply pull the end(s) of the flexible member (e.g., the ends of the loop) at the suture anchor 190 to adjust the length of the flexible member 180 extending towards the press-fit fastener 100. The flexible member 180 may also have a sliding knot (not shown). In such embodiments, the suture anchor 190 can be coupled to the press-fit fastener 100 by sliding the knot along the flexible member 180 until it is secured onto the press-fit fastener 100 with the desired tension.

It is important to note that the suture anchor 190, flexible member 180, and press-fit fastener 100 can be made from a variety of materials. For example, some or all of the components can be made from a bioabsorbable material. Alternatively, some or all of the components can be made from a bio-compatible metal (e.g., titanium) or material (such as a polymer, or bone). For example, the suture anchor 190 and flexible member 180 can be titanium and the press-fit fastener 100 can be a bioabsorbable material. The desired application will determine the most appropriate material for each component.

Additionally, the flexible member 180 can be a single strand of material or it can be made from multiple strands that are braided or otherwise formed as a single element. For example, the flexible element 180 can be fiber-wire, ultra-braid, or dura-braid, to name but a few.

Figure 10A:
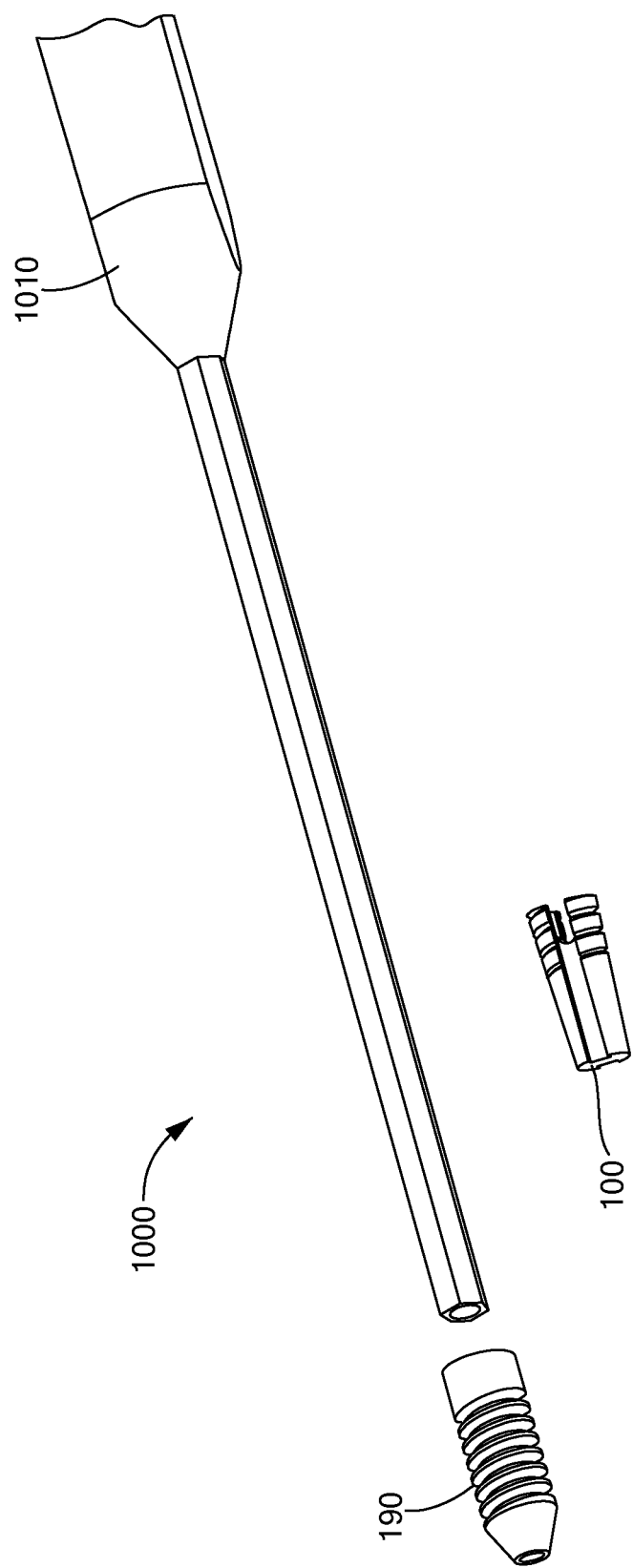
FIG. 10A schematically shows a pre-loaded kit containing the device shown in FIG. 1 and additional components, in accordance with embodiments of the present invention.
Figure 10B:
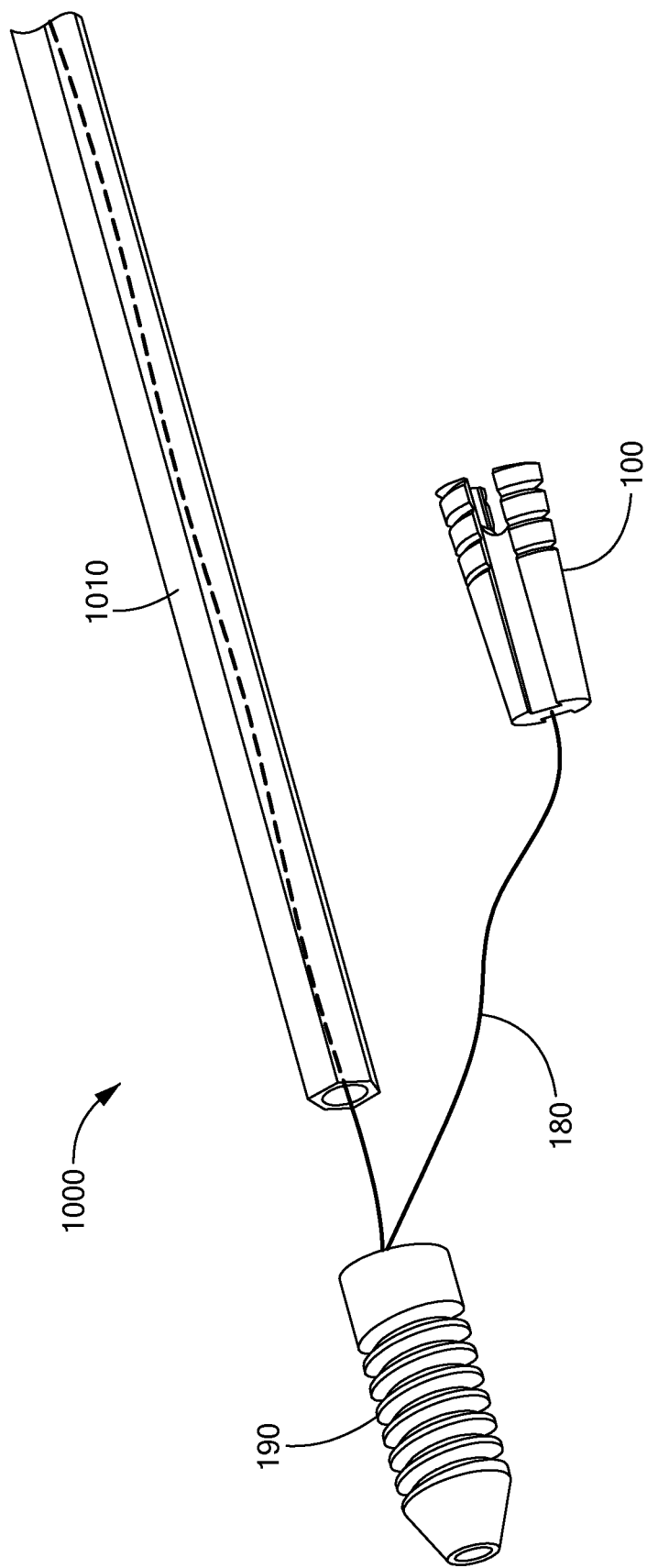
FIG. 10B schematically shows a close-up of the suture anchor and flexible element within the kit shown in FIG. 10A, in accordance with embodiments of the present invention.

In accordance with other embodiments of the present invention, some or all of the above described components can be pre-packaged in a kit 1000. For example, as shown in FIGS. 10A and 10B, the kit 1000 may include a suture anchor 190, a press-fit fastener 100, a flexible member 180, and a handle 1010. Both the handle 1010 and the suture anchor 190 may be cannulated. In some embodiments, the handle may be disposable.

Additionally, some or all of the kit components may be pre-attached (e.g., "pre-loaded") such that much of the prep work is completed for the user. In particular, the flexible element 180 may extend from the handle 1010, through the suture anchor 190, and the distal end of the flexible element 180 may be secured (e.g., coupled) to the press-fit fastener 100. For example, the distal end of the flexible element 180 may be looped over the press-fit fastener 100 (e.g., similar to a noose) or, if the press-fit fastener 100 has a central bore 160, the flexible element may be passed through the central bore 160 and tied off at the back of the press-fit fastener 100.

When using the kit 1000, the user/physician may use the handle 1010 to insert the suture anchor 190 into the drilled hole and secure the suture anchor 190 within first bone. In some embodiments, the suture anchor 190 may be threaded, tapped or otherwise engaged/secured within the drilled hole (e.g., using the handle 1010) to ensure a secure fit. The flexible element 180 supplied within the kit 1000 may be long enough to allow for a certain amount of "slack" between the suture anchor 190 and the press-fit fastener 100 so that the fastener 100 is able to be positioned outside of the surgical site and out of the way of the user until needed. The slack also allows the physician to introduce, engage, secure, and adjust the suture anchor 190 and the fastener 100 independently.

Once the suture anchor 190 is secure within the first bone member, the physician can disengage the handle with the drill tunnel. For example, the physician may pull the handle 1010 proximally, allowing the handle 1010 to slide along the flexible element 180 without interfering with the length of the flexible element 180. The physician may then place the press-fit fastener 100 into the hole in the second bone and engage the fastener 100 with the second bone. The physician may then pull the flexible element 180 (e.g., at the handle 1010) towards the physician. As the physician pulls the flexible element 180, the fastener 100 is drawn distally towards the suture anchor 180, further enforcing the press-fit and thereby adjusting the tension of the flexible element 180. The flexible element 180 may then be secured such that the length is fixed. The locking method used to secure the flexible element 180 is dependant on the type of suture anchor being used and included in the kit 1000.

Although the kit 1000 is described above as including the suture anchor 190, the fastener 100, the handle 1010 and the flexible element 180, the kit can be packaged with any number of the components. For example, the kit 1000 may include only a suture anchor 190 and a fastener 100 (e.g., not the handle 1010 and flexible element 180). Alternatively, the kit 1000 may include the suture anchor 190, the fastener 100, and the flexible element 180 (e.g., not the handle 1010).

As shown in FIGS. 11A-11B, to further simplify the use of the present invention, the fastener 100 can be used in conjunction with a cannulated and/or self-tapping suture anchor 1110. During the medical procedure, the physician may properly align the joint in question (e.g., using the K-wire joysticks described above) and then drill a guide wire 1120 through the bones (e.g., the scaphoid 610 and the lunate 620. Once the guidewire 1120 is in place, the physician can align the joint further and define exactly where the implants should be placed.

Once the locations are determined, the physician may drill out the scaphoid 610, as described above with respect to FIG. 9. For example, the physician may use a single drill to drill out only the scaphoid or may used a stepped drill to drill out both the scaphoid and the lunate. If the suture anchor is self-tapping, then the physician does not need to drill out the lunate 620 (e.g., only the scaphoid 610 needs to be drilled out). Next, because the suture anchor 1110 is cannulated, the physician need only slide (e.g., using the handle/inserter described above) the suture anchor 1110 over the guide wire and secure the cannulated suture anchor 1110 into the lunate 620 by screwing the suture anchor into the lunate 620. It is important to note that the proximal end of the cannulated suture anchor 1110 should be below the cortex of the lunate 620 so that the suture anchor is not 1110 protruding into the joint.

Once the cannulated suture anchor is in place and secured, the physician may then insert the press-fit fastener 100. If the fastener 100 is cannulated as shown in FIGS. 11A and 11B, the physician may simply slide the fastener 100 over the guide wire and use the handle/inserter to push it into the scaphoid 610. If the fastener is not cannulated, the physician must first remove the guide wire 1120 prior to inserting the fastener 100. Once the fastener 100 is inserted into the scaphoid, the physician may then secure the flexible element 180 to the fastener 100, as described above.

Figure 12A:
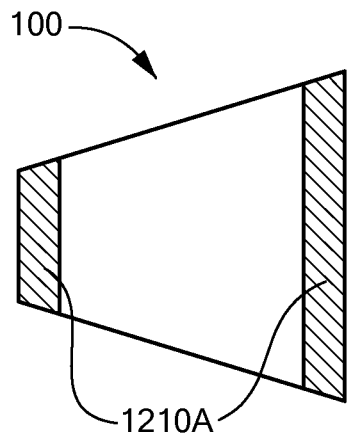
FIGS. 12A to 12D schematically show alternative embodiments of the press-fit fastener with radio-opaque markers, in accordance with embodiments of the present invention.
Figure 12B:
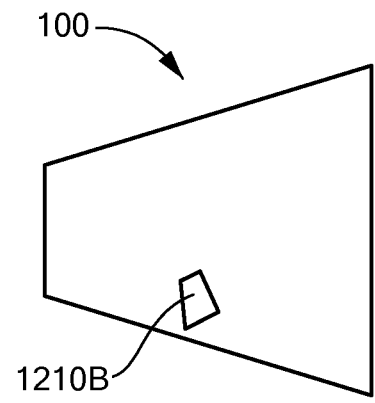
Figure 12C:
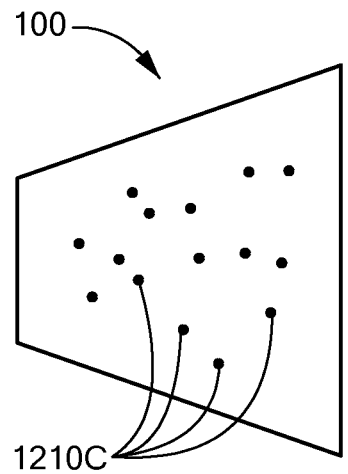
Figure 12D:
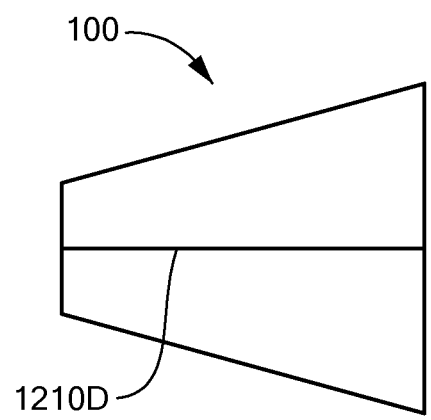

As shown in FIGS. 12A-12D, some embodiments of the press-fit fastener 100 can include radio-opaque markers 1210A-D that allow a physician to easily locate the device when taking an x-ray of the joint in question. For example, if a patient with the above described devices returns to the physician and complains of pain, the physician need not resort to surgery to view the location and status of the implants. Rather, the physician may simply take an x-ray of the joint in question. If the implant is made from a non-metallic material (e.g., PEEK, PLLA, etc.), the implant will not appear on the x-ray image. However, the radio-opaque markers 1210A-D will allow the physician to easily locate the implant (e.g, the fastener 100). The markers 1210A-D can be any of a variety of materials and structures. For example, the markers can be rings 1210A located at either end of the fastener (FIG. 12A), a single chip 1210B located at a known or random location within the fastener 100 (FIG. 12B), metallic dust particulates 1210C dispersed through the non-metallic material (FIG. 12C), or a rod 1210D through the fastener 100 along the longitudinal axis (FIG. 12D).

Figure 13:
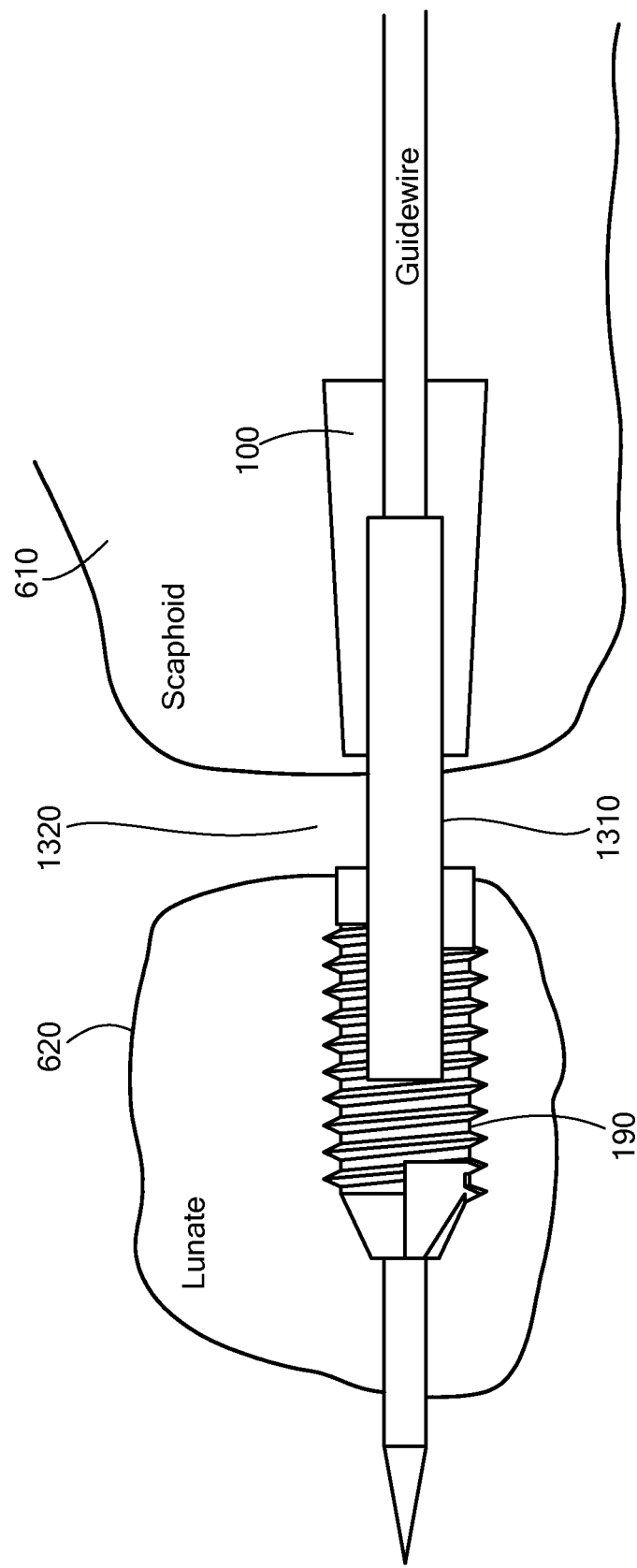
FIG. 13 schematically shows an alternative embodiment of a system with a soft-tissue implant, in accordance with embodiments of the present invention.

As mentioned above and as shown in FIG. 13, embodiments of the present invention may also include a soft tissue implant 1310 (e.g., an autograft, allograft, xenograft, or similar material). The soft tissue implant 1310 may be instead of or in addition to the flexible element 180 described above. The soft tissue implant 1310 may be secured across the joint space 1320 between the fastener 100 and the suture anchor 190. The soft tissue implant 1310 may be held within each bone using an interference fit, may be attached to the suture anchor 190 via the flexible element 180 and secured to the fastener 100 using an interference fit, or may be secured to both the fastener 100 and the suture anchor 190. To prevent damage from the threads of the suture anchor 190, the soft tissue implant 1310 may be braided with high strength suture, such as Fiberwire.

Although embodiments of the present invention are described above with respect to the scaphoid and lunate bones, embodiments of the present invention can be used in any scenario in which there is a limited amount of relative axial movement between the components. For example, embodiments of the present invention may be used to secure bones located within the foot and other non-fractured and fractured bones. As shown in FIGS. 11A-11C, some embodiments of the press-fit fastener.

Although various exemplary embodiments of the invention have been disclosed, it should be apparent to those skilled in the art that various changes and modifications can be made that will achieve some of the advantages of the invention without departing from the true scope of the invention. These and other obvious modifications are intended to be covered by the appended claims.

What is claimed is:

1. An apparatus for stabilizing joints with limited axial movement during orthopedic surgery comprising:
a fastener body having a proximal end and a distal end and configured to be press-fit into a tunnel in a first bone member, the fastener body being tapered from the proximal end to the distal end such that a width of the distal end is equal to or greater than a largest outer diameter of an at least one threaded suture anchor, the fastener body also having a proximal face that is substantially perpendicular to a longitudinal axis of the fastener body;
at least one linear channel extending from the proximal end to the distal end of the fastener body and configured to receive at least one flexible element trailing from the at least one threaded suture anchor, at least a portion of the at least one threaded suture anchor located within a second bone member; and
an indentation located within the proximal face of the fastener body, the flexible element being secured to the fastener body at the indentation.

2. The apparatus according to claim 1, wherein the linear channel extends along an outer surface of the fastener body from the proximal end to the distal end.

3. The apparatus according to claim 1, wherein the fastener body includes a central bore extending through the fastener body.

4. The apparatus according to claim 1, wherein the apparatus is titanium.

5. The apparatus according to claim 1, wherein the apparatus is made from a bioabsorbable material.

6. The apparatus according to claim 1, wherein the apparatus is made from bone.

7. The apparatus according to claim 1, wherein the fastener body includes a receptacle configured to receive a driver.

8. The apparatus according to claim 1, wherein the first bone member is a scaphoid bone and the second bone member is a lunate bone.

9. The apparatus according to claim 1, wherein the first bone member is a lunate bone and the second bone member is a scaphoid bone.

10. The apparatus according to claim 1, wherein the fastener body includes at least one thread configured to facilitate removal of the apparatus from, or adjust the apparatus within, the first bone member.

11. The apparatus according to claim 1, wherein the at least one threaded suture anchor is cannulated.

12. The apparatus according to claim 1, wherein the at least one threaded suture anchor is self-tapping.

13. The apparatus according to claim 1, further comprising a soft tissue implant secured to the at least one threaded suture anchor at a first end and the fastener at a second end.

14. The apparatus according to claim 1, wherein the fastener includes a radio-opaque marker.

15. The apparatus according to claim 1, wherein the indentation is a concavity.

16. The apparatus according to claim 1, wherein the flexible element is secured to the fastener body at the indentation by at least one of knotting, capping, crimping, brazing, and welding the flexible element.

17. The apparatus according to claim 1, wherein the at least one linear channel provides a recess for receiving the flexible element, thereby preventing interference and abrasion from surrounding bone.

18. The apparatus according to claim 1, wherein the fastener body has a substantially smooth outer surface.

19. A kit for use during orthopedic surgery to stabilize joints with limited axial movement comprising:
an at least one threaded suture anchor for insertion into a first bone member, the at least one threaded suture anchor having a largest outer diameter;
a fastener having a fastener body and at least one linear channel extending from a proximal end to a distal end of the fastener body, wherein the fastener is configured to be press fit into a hole in a second bone member, the fastener body being tapered from the proximal end to the distal end such that a width of the distal end is equal to or greater than the largest outer diameter of the at least one threaded suture anchor, the fastener also having a proximal face that is substantially perpendicular to a longitudinal axis of the fastener and an indentation located within the proximal face; and an at least one flexible element with a first end and a second end, wherein the first end of each of the at least one flexible element is attached to the at least one threaded suture anchor and the second end of each of the at least one flexible element is configured to be secured to the fastener body at the indentation, the linear channel configured to receive at least a portion of the flexible element, thereby placing the at least one suture anchor in tension and coupling the first and second bone members.

20. The kit according to claim 19, wherein the first bone member is a scaphoid bone and the second bone member is a lunate bone.

21. The kit according to claim 19, wherein the first bone member is a lunate bone and the second bone member is a scaphoid bone.

22. The kit according to claim 19, wherein the linear channel extends along an outer surface of the fastener body from a proximal end to a distal end.

23. The kit according to claim 19, wherein the linear channel is integral to the fastener body.

24. The kit according to claim 19, wherein the fastener further comprises a central bore extending through the fastener body.

25. The kit according to claim 19, wherein the fastener is titanium.

26. The kit according to claim 19, wherein the at least one threaded suture anchor is titanium 27. The kit according to claim 19, wherein the fastener is made from a bioabsorbable material.

28. The kit according to claim 19, wherein the at least one threaded suture anchor is made from a bioabsorbable material.

29. The kit according to claim 19, wherein the fastener is made from bone.

30. The kit according to claim 19, wherein the fastener body includes a receptacle configured to receive a hexagonal driver.

31. The kit according to claim 19, wherein the fastener body includes at least one thread configured to allow the apparatus to be removed from the second bone member.

32. The kit according to claim 19, further comprising a stepped drive configured to insert and remove the fastener into the second bone member.

33. The kit according to claim 19 wherein the threaded suture anchor is cannulated.

34. The kit according to claim 19, wherein the fastener includes a radio-opaque marker.

35. The kit according to claim 19, wherein the kit is preloaded and includes a soft-tissue implant.

36. The kit according to claim 35, wherein the soft-tissue implant is secured across a joint space between the threaded suture anchor and fastener.

37. The kit according to claim 19, wherein the fastener body has a substantially smooth outer surface.

* * * * *